United States Patent [19]

Bono et al.

[11] Patent Number: 5,630,409
[45] Date of Patent: May 20, 1997

[54] NEBULIZER AND INHALATION DEVICE CONTAINING SAME

[76] Inventors: Michael Bono, 882 Black Rd., Collegeville, Pa. 19426; Gary Ruff, 549 Astor Sq., West Chester, Pa. 19380

[21] Appl. No.: 409,360

[22] Filed: Mar. 22, 1995

Related U.S. Application Data

[63] Continuation-in-part of Ser. No. 409,259, Mar. 22, 1995, Pat. No. 5,611,332.

[51] Int. Cl.⁶ .................................................. A61M 16/00
[52] U.S. Cl. ....................... 128/200.18; 128/204.18; 128/205.12; 128/205.24; 128/910; 128/909; 128/200.14; 128/205.29
[58] Field of Search .................... 128/204.18, 205.12, 128/205.24, 911, 912, DIG. 26, 910, 909, 200.21, 200.18, 200.14, 205.29, 204.13

[56] References Cited

U.S. PATENT DOCUMENTS

| | | | |
|---|---|---|---|
| 4,094,317 | 6/1978 | Wasnich | 128/194 |
| 4,159,803 | 7/1979 | Cameto et al. | 239/102 |
| 4,177,945 | 12/1979 | Schwartz et al. | 239/338 |
| 4,190,046 | 2/1980 | Virag | 128/200.21 |
| 4,612,926 | 9/1986 | Boiarski et al. | 128/200.21 |
| 4,629,590 | 12/1986 | Bagwell | 261/78.2 |
| 4,767,576 | 8/1988 | Bagwell | 261/16 |
| 4,823,784 | 4/1989 | Bordoni et al. | 128/200.14 |
| 5,036,840 | 8/1991 | Wallace | 128/200.21 |
| 5,063,921 | 11/1991 | Howe | 128/200.14 |
| 5,186,166 | 2/1993 | Riggs et al. | 128/203.15 |
| 5,235,969 | 8/1993 | Bellam | 128/200.18 |
| 5,259,370 | 11/1993 | Howe | 128/200.14 |
| 5,284,160 | 2/1994 | Dryden | 128/911 |
| 5,301,662 | 4/1994 | Bagwell et al. | 128/200.14 |
| 5,309,900 | 5/1994 | Knoch et al. | 128/203.12 |
| 5,335,860 | 8/1994 | Hieftje et al. | 239/469 |
| 5,458,135 | 10/1995 | Patton et al. | 128/200.14 |
| 5,474,059 | 12/1995 | Cooper | 128/200.22 |
| 5,503,139 | 4/1996 | McMahon et al. | 128/200.18 |

FOREIGN PATENT DOCUMENTS 319067 3/1957 Switzerland ..................... 128/203.29

OTHER PUBLICATIONS

Atomic Products Corporation trade literature entitled "Venti- Scan II—Disposable Radioaerosol System For Ventilation Scanning Studies", Atomlab Division, Shirley, New York (undated).
Cadema trade literature entitled "AeroTech I—Aerosol delivery systems for improved imaging and controlled deposition of aerosol solutions", Cadema Medical Products, Inc. (undated).
International CIS trade literature entitled "Venticis II—Lung Scintigraphy Without Constraint", Subsidiary of Compagnie ORIS Industrie S.A., Saint-Quentin-Yvelines Cedex, France (undated).
Medi Nuclear trade literature entitled "Aero/Vent—Lung Aerosol Delivery System", Medi Nuclear Corporation, Inc., Baldwin Park, California, Oct. 1988.
Mallinckrodt trade literature entitled "Radioaerosol Inhalation Imaging—An Emerging Choice for the Assessment of Pulmonary Function", Diagnostic Products Division of Mallinckrodt, Inc., St. Louis, Missouri (undated).
3M trade literature entitled "It's Not Just An Air Filter, It's An Obstacle Course", 3M Filtration Products, 3M Company, St. Paul, Minnesota, 1992.

*Primary Examiner*—Vincent Miller
*Assistant Examiner*—William J. Deane, Jr.
*Attorney, Agent, or Firm*—Duane Morris & Heckscher

[57] ABSTRACT

Improved nebulizers and aerosol inhalation devices including these nebulizers are provided by this invention. The disclosed nebulizers are suitable for supplying an aerosol mist to a patient and include a liquid inlet for receiving a liquid, a gas inlet for receiving a pressurized gas and an aerosol outlet for providing an aerosol mist. An important aspect of this invention is the addition of gas swirling means or flow controlling means for creating a swirling action or a tangential velocity to the gas forming the aerosol. The nebulizer and other devices of this invention can produce an aerosol mist having an obscuration of at least 10% and a median droplet size of less than 1 μm.

23 Claims, 4 Drawing Sheets

NEBULIZER AND INHALATION DEVICE CONTAINING SAME

CROSS REFERENCE TO RELATED APPLICATIONS

This application is a continuation-in-part of U.S. patent application Ser. No. 08/409,259, filed on Mar. 22, 1995, now U.S. Pat. No. 5,611,332 and entitled "AEROSOL INHALATION DEVICE CONTAINING A RAIN-OFF CHAMBER."

FIELD OF THE INVENTION

This invention relates to methods of producing aerosols for patients, and in particular, to apparatus for improving the delivery of aerosol therapeutics and diagnostics.

BACKGROUND OF THE INVENTION

Aerosol inhalation equipment is often used in medical facilities for generating aerosol mists for diagnostic and therapeutic procedures. Such devices are especially useful in pulmonary therapy for pneumonia and for introducing radioactive vapors for diagnosing diseases.

The engine of most aerosol-generating equipment is the nebulizer, a device which mixes pressurized air or oxygen with diagnostic or therapeutic fluids to create an aerosol mist. During operation, the liquid to be aerosolized is placed in a liquid reservoir in the nebulizer. Air under pressure enters the system and acts to draw the liquid up a delivery tube to an aerosol exit orifice, similar to a jet pump. At the aerosol exit orifice, the fluid is atomized into a fine mist. Larger drops that are produced in the mist impinge on baffles above the aerosol exit orifice where they drain back into the reservoir of the nebulizer. Smaller drops are entrained by the air and are carried through the delivery system to the patient's lungs. A typical nebulizer is disclosed in Bordoni et al., U.S. Pat. No. 4,823,784.

The overall effectiveness of a nebulizer depends largely upon the distribution and size of the droplets produced. Droplets larger than 3.5 micrometers generally do not leave the nebulizer and run back into the bowl to be atomized again. Droplets between about 1.5 and 3.5 micrometers often collect on the walls of the delivery system and frequently settle onto the lips, mouth, or bronchial tubes of the patient without ever reaching the alveolar, often referred to as the "deep lung".

A 1987 study performed on one aerosol inhalation system indicated that only 25% of the liquid initially charged into the nebulizer actually reached the patient's lungs during a seven minute exposure. Typically, only 66% of this amount actually remains in the deep lung of the patient; the other 33% is exhaled. Therefore, only about 16% of the liquid therapeutic or diagnostic substance charged to the nebulizer is ever used by the patient. The remainder is wasted, or winds up contaminating the environment. Consequently, much of the liquid charge loaded into the nebulizer is provided only to ensure that a proper dose can be received in a reasonable exposure time.

Since most aerosol inhalation devices are currently made for one-time patient use, and are thereafter disposed, any medication or diagnostic fluid remaining in the device becomes waste. Nevertheless, decreasing the amount of fluid required for delivering a prescribed amount to a patient's lung while increasing the delivery efficiency of the fluid has been hard to achieve. With respect to radioactive therapeutics and diagnostics, there is also a great need to decrease the treatment times so as to minimize radiation doses to both the patient and nearby healthcare workers.

Despite these recognized deficiencies of current nebulizer devices, there has been very little improvement in the actual performance of modern systems. Most of the more recent variations have been in the nebulizer design, such as the placement of baffles, variations in orifice size and other structural elements which are somewhat unrelated to increased delivery. There has been very little research conducted to improve the particle size distribution and control through nebulization techniques rather than through baffling. There has also been few changes made in the recovery of medication and trapped moisture to reduce waste, and to improve production efficiency.

Even though modern investigators have presently correlated the mass-median-drop size (MMD) produced by a nebulizer to the properties of the liquid and the delivery system, there is currently no way to account for the effect of structural variations on the drop size produced. Moreover, previous studies have also shown that various commercial nebulizers produce essentially the same aerosol, but the structural differences between the nebulizers, such as the addition and placement of a baffle, caused selective losses of larger particles. This method of drop size reduction, by itself, is generally unsatisfactory and inefficient because the drop size is reduced at the expense of reducing the rate of drug delivery.

SUMMARY OF THE INVENTION

This invention provides a nebulizer for use in an aerosol inhalation device for supplying an aerosol mist to a patient. The nebulizer includes a liquid inlet for receiving a liquid and a gas inlet for receiving a pressurized gas. The gas and liquid are combined to provide an aerosol mist through an aerosol outlet in the nebulizer. In order to provide a higher rate of droplets delivered to a patient's deep lung, the nebulizer of this invention includes means for redirecting the pressurized gas to create a swirling action and shear force so that greater atomization of therapeutic or diagnostic liquids can be accomplished without a loss in liquid delivery efficiency.

While previous nebulizer designs were limited to jetting or venturi effect techniques to produce an aerosol, the swirling motion produced by the nebulizers of this invention produces a shear force on the liquid that is greater than that developed when the air flows straight through the orifice. When these high shear forces act on liquid therapeutics, for example, the amount of medicine delivered to the patient for a given treatment time is improved and an aerosol consisting of smaller drops is produced.

The devices of this invention can increase the rate of delivery of the droplets within the desired size range of 0.5–1.5 micrometers, while reducing the number of larger drops, e.g. above about 3 micrometers, that impact on the baffle and fall back into the reservoir. Since a larger fraction of the liquid directly produces drops within the size range most likely to be used by the patient, the initial charge of liquid in the nebulizer and the exposure time to the patient and healthcare workers can be dramatically reduced without sacrificing liquid delivery.

This invention also provides a nebulizer having a liquid reservoir for storing a prescribed liquid and a gas inlet for receiving a pressurized gas. Connected to the gas inlet of this embodiment is a venturi tube for providing an axial jet velocity to the pressurized gas. The venturi tube has a conical cross-section with a larger opening at one end of the tube and a smaller opening at the other end. Located within the venturi tube is a gas deflection member for providing a tangential velocity to the pressurized gas. This nebulizer also includes a fluid conduit providing passage of a portion of the prescribed liquid from the liquid reservoir to a point located distally from the venturi outlet opening upon the production of a vacuum by the venturi tube. A baffle is also included distally from the venturi tube outlet opening for contacting the aerosol mist and reducing the amount of droplets in the mist which exceed about 3 micrometers. Following contact with the nebulizer baffle, the aerosol mist exits an aerosol outlet, which can be connected to a conduit of an aerosol inhalation device. The nebulizer of this embodiment provides an aerosol mist having an obscuration rating of at least about 10% and a median droplet size of less than 1 micrometer.

A BRIEF DESCRIPTION OF THE DRAWINGS

The accompanying drawings illustrate preferred embodiments of the invention, as well as other information pertinent to the disclosure, in which:

FIG. 1: is a side elevation view of a preferred aerosol inhalation device of this invention, illustrating some of the more important connections and features in phantom, and the substance recovery media in cross-section;

FIG. 2: is a top planar view of the aerosol inhalation device of FIG. 1;

FIG. 3: is a side elevation, exploded view of the proximal end of the aerosol inhalation apparatus of FIG. 1; and FIG. 4: is a side elevation, cross-sectional view of a preferred nebulizer design for use in connection with the preferred aerosol inhalation apparatus of FIG. 1.

DETAILED DESCRIPTION OF THE INVENTION

Improved nebulizers for creating aerosol mists and aerosol inhalation devices containing these nebulizers are provided by this invention. These devices employ improved nebulization techniques for providing increased sheer action during atomization of therapeutic and diagnostic fluids so that a greater delivery rate of smaller liquid droplets are provided to the deep lung of patients.

Figure 1:
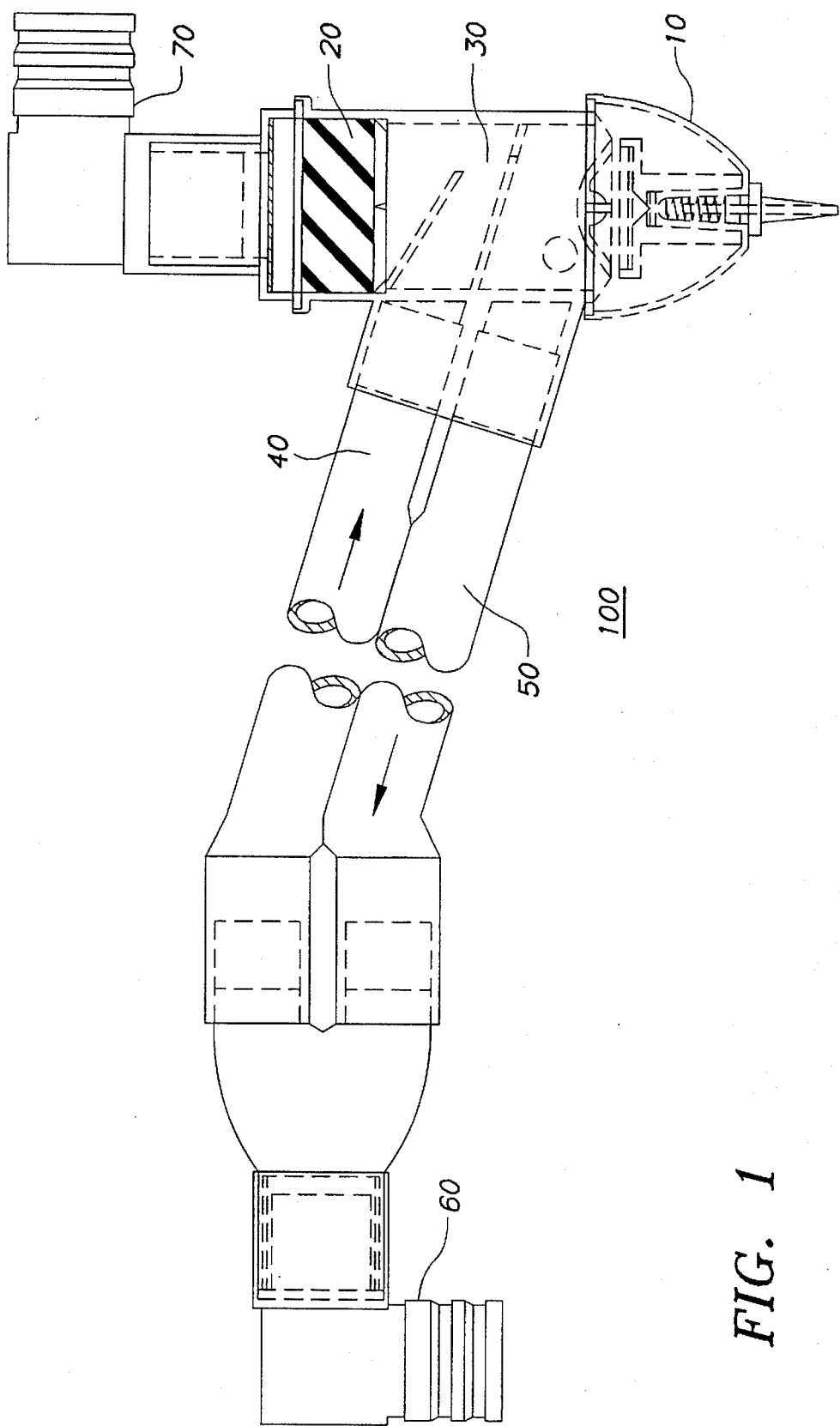
Figure 2:
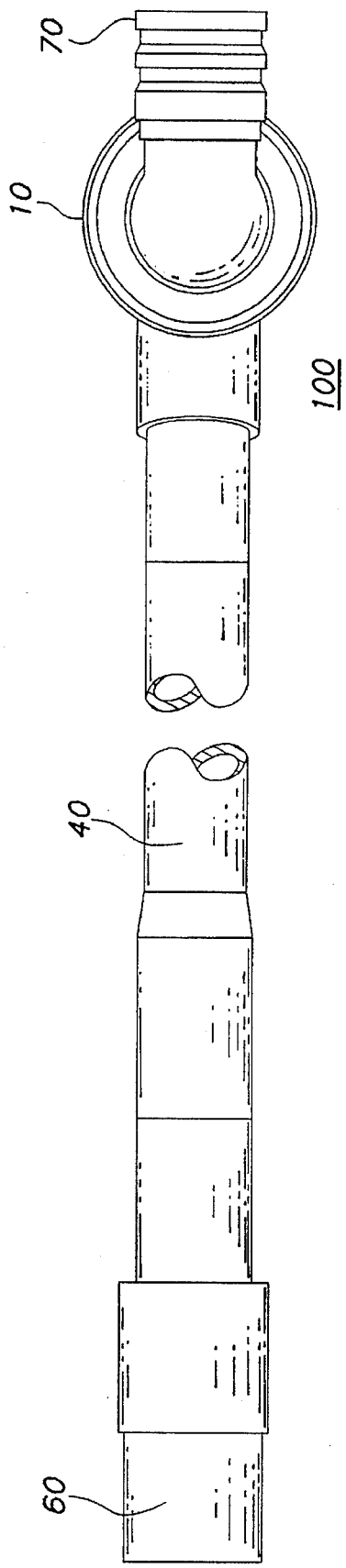
Figure 3:
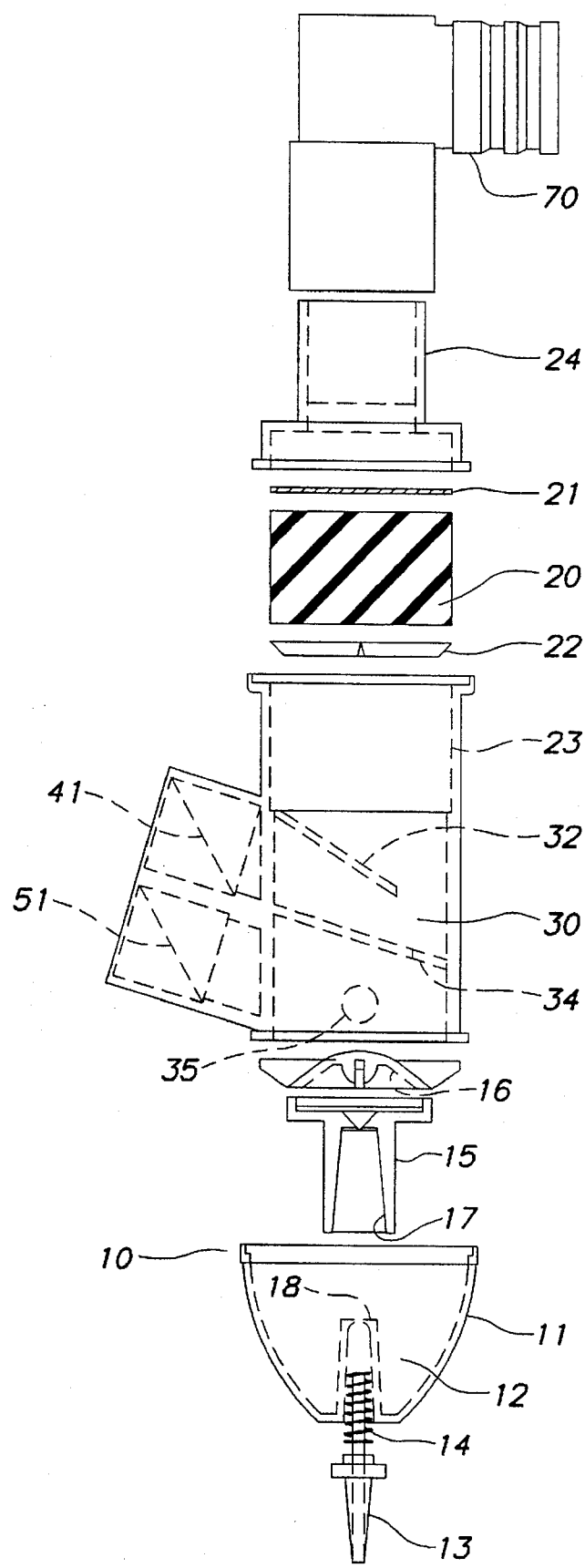

With respect to the figures and particularly with respect to FIGS. 1-3 thereof, there is shown a preferred aerosol inhalation device. This device 100 contains some basic elements which represent groups of constituent parts that are labeled together for convenience. These elements include a nebulizer 10 for producing an aerosol and an exhaust port 70 for exit gases, a form of substance recovery media 20, and a rain-off chamber 30 which helps to contain humidity and recycle expensive therapeutic and diagnostic fluids back into the nebulizer 10. As the patient breathes through a mouthpiece attached to the fitting 60 located at the distal end of the device 100, aerosol mist and compressed air are received through one-way valve 51 and aerosol conduit 50. As the patient exhales, one-way valve 51 closes, one-way valve 41 opens, and exhaust gases are channeled through exhaust conduit 40 into the rain-off chamber 30 where aerosol, water vapor, liquid and gases are separated. Liquid constituents are returned to the nebulizer by gravitational force, exhaust gases are discharged, and any left-over aerosol is temporarily stored in the chamber 30. When the patient inhales a second, or subsequent, time, droplets contained within the substance recovery media 20 are returned to the nebulizer or are returned back to the patient through one-way valve 51.

The operational parts of these basic elements will now be described in more detail.

With reference to the exploded view of FIG. 3, compressed air or oxygen is typically received through the gas inlet 13 at the proximal end of the nebulizer 10. A compressor can be attached to the nipple of the gas inlet 13 to generate a source of compressed air at a pressure of about 35-50 psi and a flow rate of less than about 10 liters per minute, and preferably about 6 liters per minute.

Figure 4:
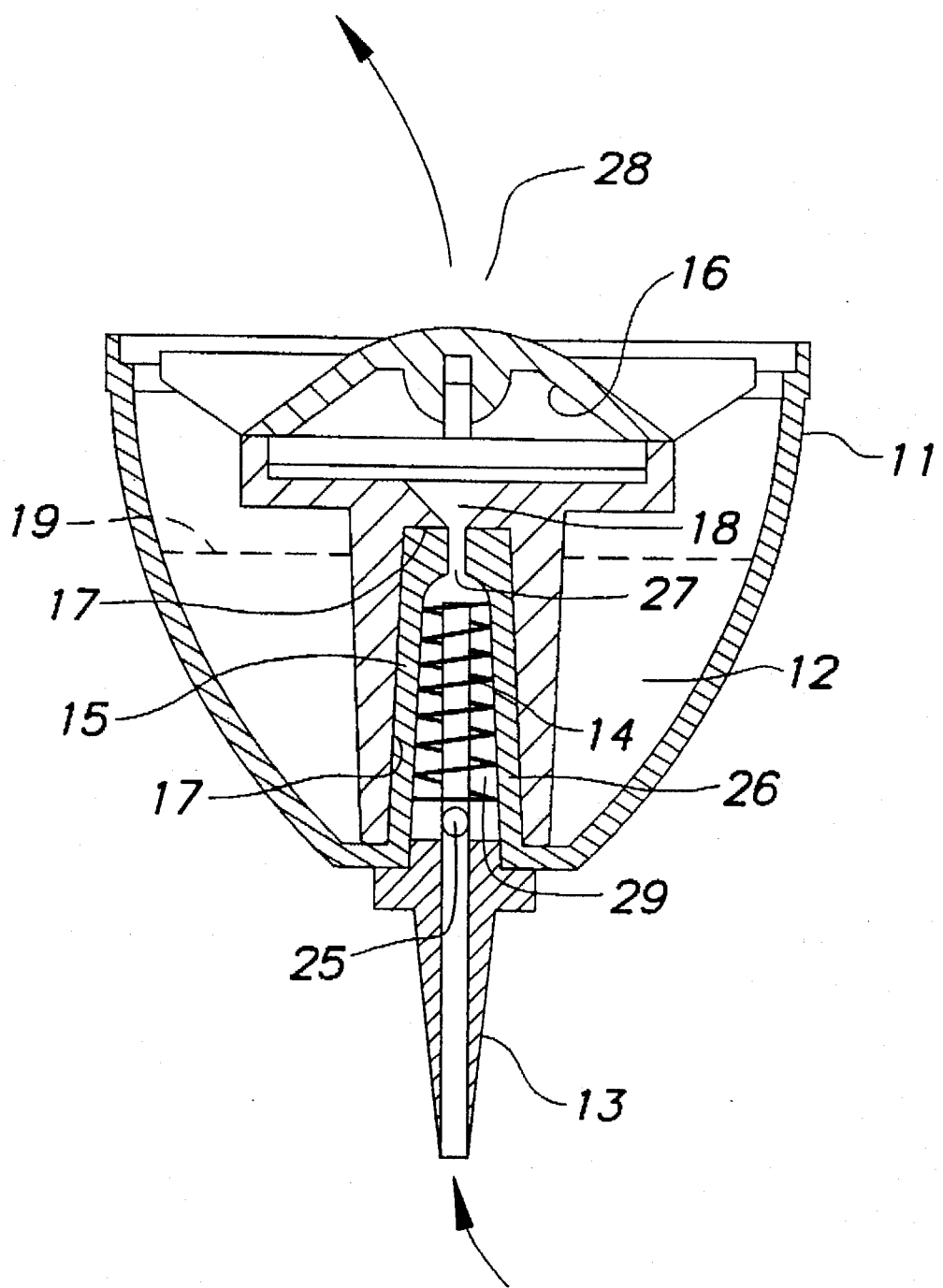

Once the air comes through the gas inlet 13 and through gas channel inlet orifice 25, it contacts a gas flow control device, which in the preferred embodiment, provides both an axial jet velocity and a tangential velocity to the gas. This can be accomplished by a combination of a swirler 14 and gas channel wall 26, shown more clearly in FIG. 4. The swirler 14 preferably consists of a spiral air passage, although there are many other ways to produce a swirling action, such as by employing vanes, a propeller-device, or inner helical grooves mounted within the gas channel wall 26.

The gas channel wall 26 preferably is in the shape of a venturi tube so as to provide an axial jetting velocity to the compressed gas. When the swirler 14 and venturi tube are used together, a high delivery rate aerosol can be produced because the normal breakup of liquid caused by the axial jetting action is enhanced by the swirling air flow, and more shearing forces are created, providing more efficient atomization. The result is that more smaller drop sizes are produced at the same overall liquid delivery flow rates as provided by existing nebulizers.

The nebulizer 10 also includes a bowl housing 11 for containing a liquid reservoir 12. The liquid reservoir is charged to a liquid level 19 located below the deflector dome 16. As compressed air flows through the gas channel 29 formed between the gas channel wall 26 and swirler 14, it is deflected by the helical ridges of the swirler 14 in a tangential direction to produce a tangential velocity element to the jet flow. The swirling gases then exit at the gas channel exit orifice 27 and create a venturi vacuum. This vacuum, in turn, draws liquid from the liquid reservoir 12 through liquid channel 17 formed between liquid channel insert 15 and gas channel wall 26, which mixes with the swirling gas jet at the liquid channel orifice 18 to form an aerosol.

Within a fraction of a second, the aerosol contacts the lower surface of the deflector dome 16, which collects droplets larger than about 3-3.5 micrometers and returns them back into the liquid reservoir 12 along the wall of the bowl housing 11, so that they can be atomized later. Particles between about 1.5 and 3.5 micrometers can also collect along the bowl housing 11 and be returned in similar fashion. The aerosol, thus produced, exits the aerosol outlet 28 and is channeled through the one-way valve 51 into the aerosol conduit 50 and to the patient. Injections of additional liquid, or an additional substance, can be delivered into the liquid reservoir through injection port 35.

The aerosol produced by the nebulizer 10 of this invention preferably has an increased delivery rate of liquid drops within the size range of about 0.5-1.5 micrometers. One way of measuring the delivery rate is to pass a laser light beam, infrared radiation or an equivalent radiation source through a cloud produced by the aerosol and measure the amount of light that passes through the mist with a light detector. The reading for the amount of light that is obscured by the mist is called the "obscuration rating" of the aerosol and is directly related to the aerosol's delivery rate. The aerosols of this invention have a preferred obscuration rating of at least 10% even though they can simultaneously produce a median droplet size of less than one micrometer. This has not been accomplished in prior art devices because baffling techniques alone only serve to reduce the number of larger particles at the expense of delivery rate and obscuration rating. This is shown by the MICROCIRRUS device listed in Table 1. Current nebulizers have succeeded in improving the obscuration rating only by allowing more droplets of greater sizes to pass from the nebulizer, as illustrated by the data for the ULTRAVENT commercial nebulizer in Table 1 below. Amici's novel VENTISOL device, has succeeded in maintaining a large number of small droplets, while at the same time delivering a large volume of liquid with a high obscuration rating. A comparison of all three products is reflected below.

such as HME media produced by 3M. HME media can achieve an extremely high moisture return rate with low resistance to exiting gases. It is salt-free, so it does not leech out salts that can corrode the equipment or be recycled back into the nebulizer. It comes in thicknesses of about 18–24 mm, has a moisture output of greater than 28 mg/l at 500 ml tidal volume, and exhibits a resistance to flow of up to 2.8 cm $H_2O$ at 60 l/m.

The preferred substance recovery media 20 is disposed below a recovery media cap 24 and is sandwiched between filter 21 and snap ring 22, although it is envisioned that the filter 21 could be located more distally or proximally in the inhalation device.

The preferred filter 21 consists of thermoplastic strands of woven or non-woven material which are layered to acquire

TABLE 1

| | Comparison of Aerosols of Competitive Devices | | | | | | |
|---|---|---|---|---|---|---|---|
| | Obscuration | Median Droplet Size (50%) | % of Droplets Between .2–.48 µm | % of Droplets Between .48–.59 µm | % of Droplets Between .59–.71 µm | % of Droplets Between .71–.86 µm | % of Droplets Below 1.04 µm |
| MICROCIRRUS | 8.66% | .64 µm | 15.62 | 23.11 | 23.24 | 17.44 | 90.2 |
| ULTRAVENT | 18.97% | 1.02 µm | .03 | 5.72 | 11.55 | 15.83 | 52.0 |
| VENTISOL | 21.04% | .62 µm | 21.37 | 23.07 | 21.46 | 15.38 | 90.56 |

The preferred substance recovery media section of this invention will now be described. In certain medical breathing applications, moist air is added to the breathing circuit to prevent the patient's lungs from drying out. Since patients exhaust moisture, there is already a source of humidity available within the closed system which can be used to remoisturize a patient's own lungs. This invention provides a substance recovery media 20 located in the proximal end of the aerosol inhalation device 100, preferably between the rain-off chamber 30 and exhaust port 70.

The substance recovery media 20 should be able to achieve high moisture output with low resistance to exhaust gases. It is also desirable that it be salt- and toxic-free. The preferred substance recovery media 20 contains a fibrous material having a plurality of air channels formed therein for attracting liquid onto the fibers, while permitting gas to flow through. Such material should be able to recover moisture, including therapeutic and diagnostic liquids, as well as water vapor exhausted by the patient.

With respect to FIG. 3, the operation of the preferred rain-off chamber 30 in combination with the substance recovery media 20 will now be described. As the patient exhales, exhaust gases, including entrained medications, diagnostics, mucous, or water vapor are delivered through one-way valve 41 and into chamber 30. Liquid droplets in the gas are then tapped by the substance recovery media 20 while the gas exits exhaust port 70. Liquids collecting on the chamber walls can be returned back through the rain-off return 34 into the nebulizer 10, where they can be reatomized. Any remaining water vapor or entrained medicine in the chamber 30 can be reinhaled by the patient, back through rain-off return 34 through one-way valve 51. This process can be assisted by ambient air received through the exhaust port 70, which helps to push stalled vapors in the chamber 30 and collect and blow back captured droplets from the substance recovery media, and deliver these liquid and vaporous substances back to the patient.

Acceptable substance recovery materials include polymer- or natural fiber-based moisture exchange media, a desired filtration density of about 200 g/cm$^3$. The thermoplastic preferably is polypropylene or polyethylene, although many other polymers would be suitable.

The filter 21 can be die cut into a desired shape to fit the substance recovery form, recovery media cap 24, or both. The filter 21 should be of sufficient size and density to prevent the penetration of vapors, toxins, viruses etc., from exiting exhaust port 70. It can be electrostatically charged or treated to be hydrophilic or hydrophobic depending on the end use for the material. One preferred filtration media is a product manufactured by 3M under the trademark FIL-TRETE.

In an important aspect of the filter 21 of this invention, a seal of less than about 0.25 inch in width is provided around the filter's outer periphery. In a preferred embodiment the filter 21 can be sealed by such methods as heat sealing, ultrasonic sealing, or by applying pressure to melt the thermoplastic strands along the edge of the filter 21 to form a relatively solid mass. The filter 21 can also be sealed to fit within holding frames, filter shelves or other mechanisms to give it strength and shape to satisfy a particular filtration requirement. Other methods of sealing the periphery of the die cut edge of the filter can include using adhesive sealing materials such as wax, varnish, epoxy, or glue that would solidify the die cut edge and create a water, air flow, and vapor seal.

In many prior art filter devices, holding frames and shelves are designed with edge clamps which mechanically retain a filter in place, but allow vapor and other contaminants to pass around the die cut limits of the filter. By providing a positive adhesive or melted seal around the filter, such vapor leaks are substantially eliminated.

The sealed edge filter of the preferred embodiment has application outside of the nebulizer field, and can be useful in many applications where particle capture is critical and space is at a premium. Such applications include ventilation systems, air purifiers, air conditioners, computers, vacuum cleaners, copying machines, laser printers and other equipment. In the medical field, applications include breathing circuits, spirometers, incubator filters, radioaerosol moisture trapping devices and similar apparatus.

The rain-off chamber 30, described above, can be fabricated within the body 23 of the aerosol inhalation device 100. As shown in FIG. 3, the body 23 is preferably located between the nebulizer 10 and the substance recovery media 20. The rain-off chamber 30 is desirably positioned proximally from one-way valve 41, and one-way valve 51. During use, aerosol enters in the lower half of the rain-off chamber 30 from the nebulizer 10 and is directed through one-way valve 51 into the aerosol conduit 50 for patient use. When the patient exhales, exhaust gases and leftover aerosol vapor travel down exhaust conduit 40, through one-way valve 41, and back into the upper portion of the rain-off chamber 30. The gases, with their entrained vapors, contact the inner surfaces of the rain-off chamber 30, and the larger droplets accumulate immediately upon exhaust deflector 32 and the far wall of rain-off chamber 30 Since nearly 66% of the total amount of aerosol inhaled by the patient is passed through the exhaust conduit 40, the rain-off chamber 30 can be important in order to recycle and conserve expensive diagnostic and therapeutic liquids. When these vapors come in contact with the inner surfaces of the rain-off chamber, they condense or bead up onto the surfaces and are fed by gravitational forces downward through the rain-off return 34 and back into the liquid reservoir 12 of the nebulizer 10.

In a preferred embodiment of the rain-off chamber 30, a significant portion of the interior surfaces of this chamber 30 is hydrophobic, in that the liquid contact angle of droplets on these surfaces is less than about 90 degrees. Stated differently, the rain-off surfaces preferably have a critical surface tension of less than about 40 dyres/cm, and more preferably less than about 32 dyres/cm. Hydrophobic polymers, ceramics, cellulosic and metallic materials or other materials which have been coated to be hydrophobic can be used. Suitable materials include polyethylene, polypropylene, fluorocarbons, silicones and the like. One commercial resin that has proved to be acceptable is Exxon's Exact Resin No. 4024. Silicone rubber and polyethylene, however, appear to show the greatest promise in recycling aerosol products.

From the foregoing, it can be realized that this invention provides improved nebulizers and aerosol inhalation apparatus that contain them. These nebulizers can increase the rate of delivery of efficacious aerosol mists to the deep lung of patients by using improved nebulization techniques. Additionally, improved rain-off techniques are used to recirculate valuable therapeutic and diagnostic fluids for reatomization, and more effective substance recovery and filtration designs are disclosed for protecting the environment and returning liquid and liquid vapor back to the nebulizer or patient. Although various embodiments have been illustrated, this is for the purpose of describing, and not limiting the invention. Various modifications, which will become apparent to one skilled in the art, are within the scope of this invention described in the attached claims.

What is claimed is:

1. An aerosol inhalation device for supplying an aerosol mist to a patient, comprising:

a nebulizer having a liquid reservoir for containing a liquid, a gas inlet for receiving a pressurized gas, and an aerosol outlet;

a first conduit connected to said nebulizer and in open communication with said aerosol outlet;

a second conduit for receiving an exhaust gas from said patient;

said nebulizer further comprising gas flow controlling means for providing a swirling action to said gas prior to contacting said gas with said liquid to improve a/delivery of said liquid to the lungs of said patient.

2. The inhalation device of claim 1, wherein said gas flow controlling means comprises an inlet opening and an outlet opening.

3. The inhalation device of claim 2, wherein said gas flow controlling means comprises a venturi tube.

4. The inhalation device of claim 2, wherein said gas flow controlling means comprises gas swirling means for providing a swirling motion to said gas.

5. The inhalation device of claim 4, wherein said gas swirling means comprises a plurality of helical ridges.

6. The inhalation device of claim 5, wherein said gas swirling means comprises a conical tube concentrically disposed around said helical ridges.

7. The inhalation device of claim 6, wherein said conical tube comprises a decreasing cross-section between said inlet opening and said outlet opening.

8. The inhalation device of claim 1, wherein said gas flow controlling means comprises:

a venturi tube located between said gas inlet and said aerosol outlet for providing an axial velocity to said gas; and a gas swirling device disposed within said venturi tube for swirling said gas to provide said tangential velocity to said gas.

9. The inhalation device of claim 1 further comprising a deflector dome having a curved surface thereon for contacting an aerosol exiting from said aerosol outlet.

10. The inhalation device of claim 1, wherein said gas flow controlling means exerts shear forces on said pressurized gas to improve an atomization of said liquid.

11. The inhalation device of claim 10, wherein said swirling means produces an increase in a delivery rate of liquid droplets in said aerosol within the size range of 0.5–1.5 micrometers.

12. A nebulizer for use in an aerosol inhalation device for supplying an aerosol mist to a patient, comprising:

a liquid inlet for receiving a liquid;

a gas inlet for receiving a pressurized gas;

an aerosol outlet for providing an aerosol mist; and gas swirling means for providing a swirling action to said gas prior to contacting said gas with said liquid to form said aerosol mist.

13. The nebulizer of claim 12, wherein said gas swirling means comprises a gas deflection member having a solid axial core and a plurality of helical ridges disposed on said axial core.

14. The nebulizer of claim 12 further comprising a conical tube having a gradually reducing cross-section disposed around a portion of said swirling means.

15. The nebulizer of claim 12 further comprising a liquid channel disposed between said liquid source and said aerosol outlet.

16. The nebulizer of claim 15, wherein said swirling means comprises gas inlet and outlet portions and said liquid channel comprises a liquid outlet orifice located distally from said gas outlet portion.

17. The nebulizer of claim 16, wherein said aerosol mist has an obscuration rating of at least 10% and a median droplet size of less than 1 μm.

18. The nebulizer of claim 16, wherein said aerosol mist has at least 17% of its droplets within the size range of about 0.2–0.48 μm.

19. A method of providing an aerosol mist to a patient, comprising:

providing an aerosol inhalation device including a nebulizer having a liquid inlet for receiving a liquid, a gas inlet for receiving a pressurized gas, and an aerosol outlet for providing an aerosol mist;

a first conduit connected to said nebulizer and in open communication with said aerosol outlet;

a second conduit for receiving an exhaust gas from said patient;

said nebulizer further including gas flow controlling means for providing a tangential velocity to said gas to improve its shearing action prior to contacting said liquid;

permitting said patient to breathe said aerosol mist through said aerosol inhalation device;

said aerosol mist having an obscuration rating of at least about 10% and a median liquid droplet size of no greater than 1 µm.

20. The method of claim 19, wherein said improvement to said shearing action is created in said gas prior to contacting said liquid and forming said aerosol.

21. The method of claim 19 further comprising storing said liquid within a liquid reservoir in said nebulizer proximally from said aerosol outlet.

22. The method of claim 19, wherein said swirling means atomizes said liquid to form an aerosol having at least 17% droplets within the size range of about 0.2–0.48 µm.

23. A nebulizer for use in an aerosol inhalation device for supplying an aerosol mist to a patient, comprising:

a liquid reservoir for storing a prescribed liquid;

a gas inlet for receiving a pressurized gas;

a venturi tube connected to said gas inlet for providing an axial jet velocity to said pressurized gas, said venturi tube having:

a conical cross-section;

a larger venturi tube inlet opening located distally from said gas inlet; and a relatively smaller venturi tube outlet opening located distally from said venturi tube inlet opening;

a gas deflection member located within said venturi tube between said venturi tube inlet and outlet openings for providing a tangential velocity to said pressurized gas prior to contacting said liquid;

a fluid conduit for providing passage of a portion of said prescribed liquid from said liquid reservoir to a point located distally from said venturi tube outlet opening upon the production of a vacuum by said venturi tube;

a baffle located distally from said venturi tube outlet opening for contacting said aerosol mist and reducing an amount of droplets in said aerosol mist which exceed about 3 µm; and an aerosol outlet for connecting to a first conduit of an aerosol inhalation device;

said nebulizer providing an aerosol mist having an obscuration rating of at least 10% and a median droplet size of less than 1 µm.

* * * * *